United States Patent [19]

Hardy

[11] Patent Number: 4,981,135
[45] Date of Patent: Jan. 1, 1991

[54] THERAPEUTIC THERMAL CUFF

[76] Inventor: John F. Hardy, 1 Beech Cir., Andover, Mass. 01810

[21] Appl. No.: 367,445

[22] Filed: Jun. 16, 1989

[51] Int. Cl.⁵ .......................... A61F 7/10; A61F 7/08; A61F 7/03
[52] U.S. Cl. .................................. 128/402; 128/403; 128/379; 128/82.1
[58] Field of Search ................ 383/901; 128/402, 403, 128/379, 380, 82.1, 399; 62/530

[56] References Cited

U.S. PATENT DOCUMENTS

| | | | |
|---|---|---|---|
| 2,595,328 | 5/1952 | Bowen | 128/403 |
| 3,736,769 | 6/1973 | Peterson | 128/402 X |
| 3,893,834 | 7/1975 | Armstrong | 128/403 X |
| 4,121,582 | 10/1978 | Masso-Remiro | 128/402 X |
| 4,556,055 | 12/1985 | Bonner, Jr. | 128/402 X |
| 4,576,169 | 3/1986 | Williams | 128/402 |
| 4,596,250 | 6/1986 | Beisang, III et al. | 128/402 |
| 4,605,006 | 8/1986 | Jacques | 128/402 X |
| 4,628,932 | 12/1986 | Tampa | 383/901 X |
| 4,700,706 | 10/1987 | Munch | 128/403 |
| 4,736,088 | 4/1988 | Bart | 128/402 X |
| 4,765,338 | 8/1988 | Turner et al. | 128/402 |

FOREIGN PATENT DOCUMENTS 1185811 3/1970 United Kingdom ................ 128/402

Primary Examiner—Robert A. Hafer
Assistant Examiner—Kevin G. Rooney

[57] ABSTRACT

There is disclosed herein a therapeutic thermal cuff device for therapeutic heating or cooling treatment of the body members of humans or animals. The device comprises an envelope having interior and exterior panels defining one or more pouches adapted to receive therein packets of a heat of fusion composition. The exterior panel of the envelope comprises a thermally insulative polymer foam layer and that portion of the exterior panel overlying the pouches is quilted in a manner designed to improve the flexibility of the envelope in the direction of wrap of the cuff around the body member. The heat of fusion composition is contained in a heat sealed thermoplastic film container which is also quilted in a manner such as to segment the packet into a number of heat of fusion composition-containing chambers which are articulatingly affixed to one another so as to assure flexibility of the packet in the direction of the wrap of the cuff around the affected body member. The cuff and packets are reusable and the therapeutic thermal treatments provided thereby are of relatively long duration without repeated intervention or replacement of materials.

39 Claims, 6 Drawing Sheets

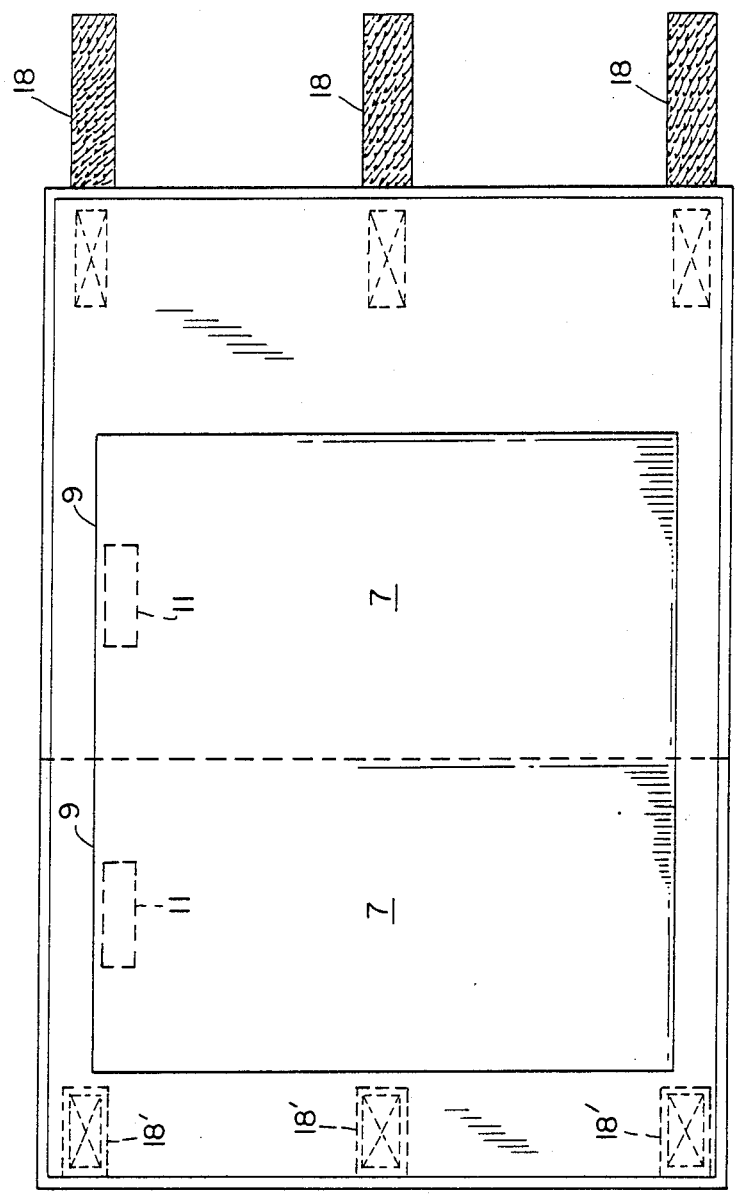

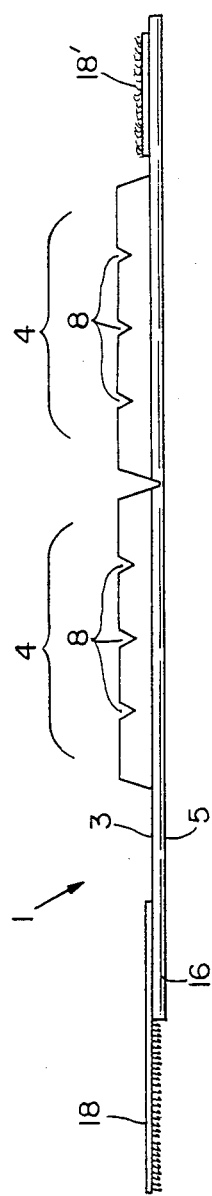
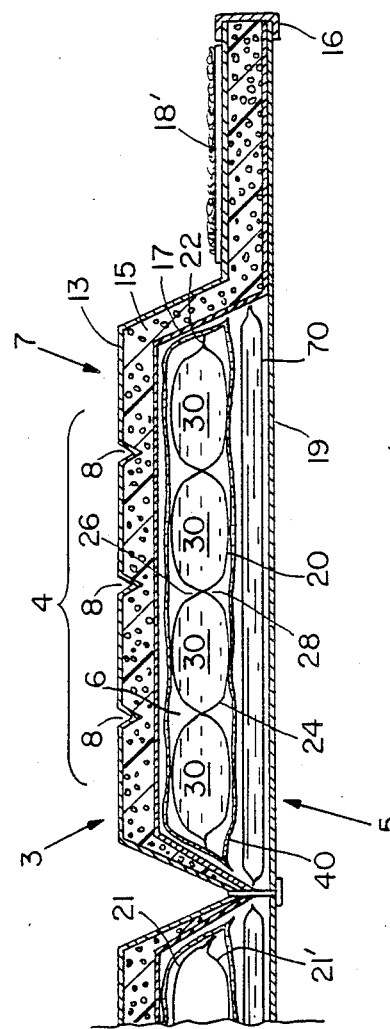

4,981,135

THERAPEUTIC THERMAL CUFF

BACKGROUND OF THE INVENTION

The present invention relates generally to therapeutic cooling or heating cuffs for human or veterinary applications and is more particularly concerned with such cuffs wherein the active cooling or heating component comprises a heat of fusion composition.

It is well known that various orthopedic human and animal maladies, such as strains, sprains, ligament and muscle tears, tendonitis, impact traumas and the like can be effectively treated by the application of heat or cold to the affected body member. While various equipments such as diathermy, ultra-sound, infra-red, whirlpool baths and similar apparatuses can deliver such thermal treatments, one of the disadvantages thereof is that, because of their bulk, weight and need for electric power, the patient, whether human or animal, must generally be transported from the site of injury or onset of the malady to the treating apparatus. In most instances, of course, it is preferable to apply the thermal treatment as quickly as possible after the onset of the malady or injury. Another problem utilizing such devices is that ambulation of the patient is usually severely restricted during treatment therewith and that, perforce, such treatment is usually measured in terms of minutes rather than for generally more therapeutically helpful periods of one or more hours. In partial response to these deficiencies various thermal packs or cuffs have been developed whereby immediate first aid treatment of injuries can be applied. Perhaps the simplest of these cuffs is a rubber tube filled with ice or hot water. The longevity of the treatment available with such cuffs is usually dictated by the mass of the water contained therein, that is to say, the smaller the mass of water contained the less the time of effective treatment available therefrom. At the very least, therefore, such water or ice filled cuffs tend to require periodic replacement of the contents with fresh ice or hot water in order to maintain the therapeutic value of the treatment and this cycle time tends to be quite short, usually on the order of fifteen minutes to about one-half hour. Other known therapeutic thermal cuffs are known wherein the active heat or cold producing component depends upon endothermic or exothermic reactions between separate and distinct ingredients which are mixed at the time of use. While temporarily effective, it is clear that such devices are capable of but a single use and that the disposal of the spent chemical packs poses a waste disposal problem or hazard.

In accordance with the present invention, however, there is provided a therapeutic thermal cuff device in which many of the above deficiencies are eliminated or substantially ameliorated.

OBJECTS OF THE INVENTION

It is a principal object of the invention to provide a novel therapeutic thermal cuff device.

It is another object of the invention or provide a device of the foregoing type wherein the thermally active component thereof is reusable.

It is still another object of the invention to provide a device of the foregoing type wherein thermal treatment of an affected body member can be achieved over a period of at least several hours without periodic replacement of the thermally active component thereof or other need for attention.

Other objects and advantages of the present invention will in part be obvious and will in part appear hereinafter.

SUMMARY OF THE INVENTION

In accordance with the invention the therapeutic thermal cuff comprises a flexible envelope having an exterior panel comprising a thermally insulative polymeric foam layer, an interior panel composed of a fabric and at least one pouch defined between the exterior and interior panels to receive a packet of thermally active material. That portion of the exterior panel overlying the pouch(es) is quilted in a pattern such as to maintain flexibility of said portion in at least the intended direction of wrap of the cuff around the body member. Received in each pouch of the envelope is a packet containing the thermally active component of the invention. The packet comprises a container formed of a heat sealed thermoplastic film material, said container also being quilted, by heat sealing thereof, in a pattern adapted to maintain flexibility in the intended direction of wrap of the cuff around the body member. Said quilting, then, defines a packet comprising a number of separate and distinct chamber, the neighboring chambers being physically and articulatingly connected to one another by a thin web of heat sealed polymeric film material. Said chambers are loaded with a heat of fusion composition having a fusion or phase change temperature within a preselected therapeutic range of interest. In use, the packets are first warmed (in the case of therapeutic heating packets) to above the fusion temperature, or cooled (in the case of therapeutic cooling packets) to below the fusion temperature, of the heat of fusion composition of the packet. The thusly heated or cooled packets are loaded into the pouch(es) of the envelope and the envelope wrapped around and secured to the affected body member with the exterior panel, comprising the insulative foam layer, outermost. In the heating embodiment of the invention the treated body member extracts sensible heat from the warmed heat of fusion composition and, as the composition cools to its fusion temperature, said composition generates heat of fusion to maintain the body member at the desired therapeutic temperature over a protracted period of time. The insulative foam layer forming an element of the exterior panel of the envelope insulates the heat of fusion composition from the cooling effect of the external environment and conserves heat generated by the heat of fusion composition within the wrapped cuff, thereby further preserving the thermal state of the treated body member, In the cooling embodiment of the invention the previously cooled heat of fusion composition extracts heat from the affected body member and, as the temperature of the heat of fusion composition rises through its fusion or phase change temperature, said composition extracts further heat from the body member, again over a protracted period. The insulative foam layer of the exterior panel of the envelope again acts to minimize the thermal load imposed on the heat of fusion composition by the external environment, thereby, in effect, forcing the composition to extract the bulk of the heat required to bring it through its fusion temperature from the body member.

DESCRIPTION OF THE DRAWING

FIG. 2 is a schematic, diagrammatic, plan view of the interior side of the therapeutic thermal cuff of FIG. 1.

FIG. 3 is a schematic, diagrammatic side view of the therapeutic thermal cuff of FIG. 1.

FIG. 4 is a schematic, diagrammatic, sectional, side view of a portion of the therapeutic thermal cuff of FIG. 1 taken through lines 4—4" thereof.

DESCRIPTION OF PREFERRED EMBODIMENTS

Figure 1:
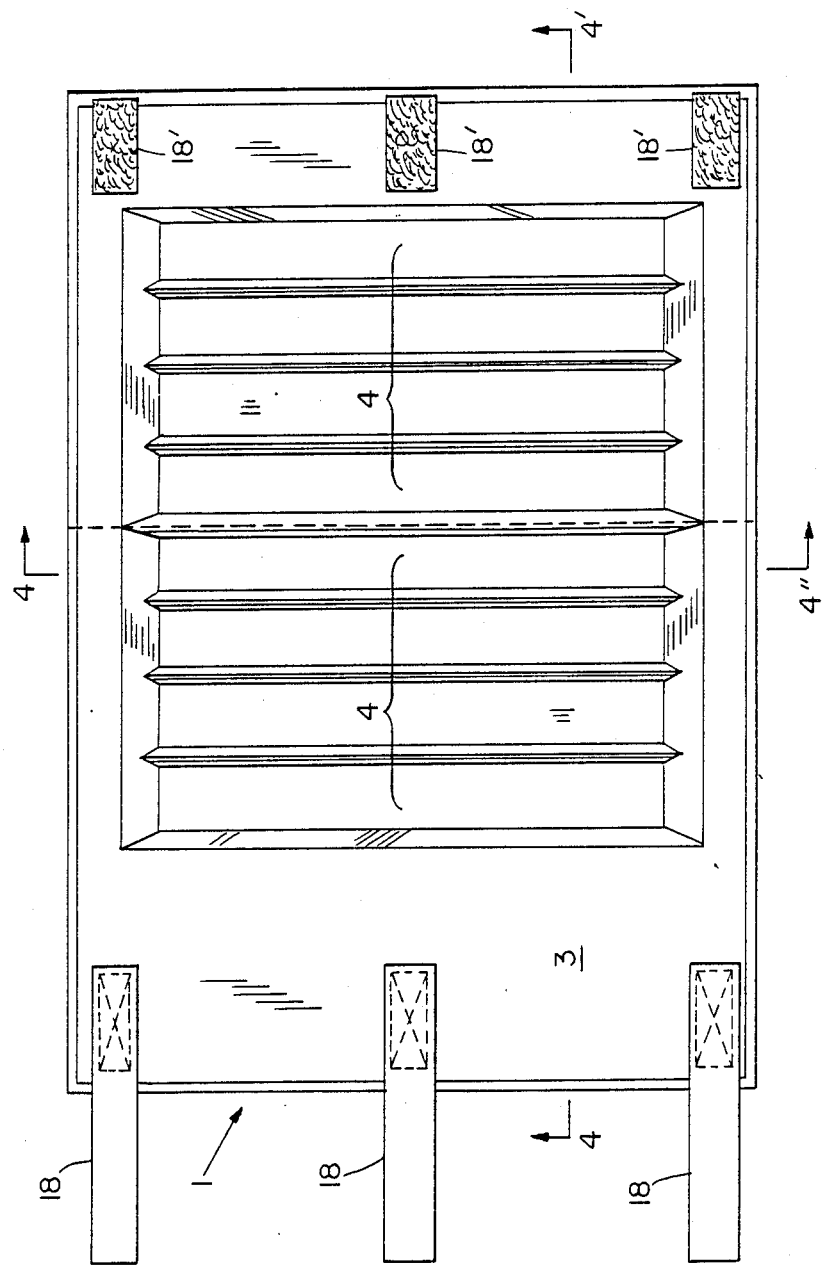
FIG. 1 hereof is a schematic, diagrammatic, plan view of the exterior side of one embodiment of the therapeutic thermal cuff of the invention.

Referring to the drawing, wherein in FIGS. 1 through 7 like reference numerals refer to like structures, and with particular reference now to FIGS. 1 through 4, the therapeutic thermal cuff device of the invention broadly comprises an envelope 1 adapted to hold therein one or more packets 20 of a heat of fusion composition 30. The envelope 1 comprises an exterior panel 3 and an interior panel 5, said panels being secured or bonded together so as to define one or more pouches 7 (FIG. 3). Each pouch 7 is provided with a slot 9 (such as through the interior panel 5) through which is received a packet 20 containing the heat of fusion composition 30. Desirably, each pouch 7 is provided with closure means 11 located in the region of slot 9, as shown in phantom in FIG. 2, and which closure means 11 may take any suitable form known in the art, such as snap fasteners, buttons, slide fasteners and the like. Preferably, however, the closure 11 will take the form of the well known hook and loop tape fastener systems exemplified by the fasteners sold under the brandname, VELCRO ® fasteners, by Velcro USA Inc., Manchester, N.H.

In order that the cuff be adequately flexible to wrap comfortably around the body member to be treated and in order that it be thermally efficient it is important that the exterior panel 3 comprises a polymeric foam insulative layer 15 and that at least that portion of said panel overlying the pouches 7 be quilted in a pattern such as to confer substantial flexibility in the wrapping direction thereof. As best shown in FIG. 4, the exterior panel 3 of envelope 1 is preferably defined by an exteriormost protective woven fabric layer 13, such as an interlocked polyester fabric, continuously bonded to the exterior surface of a layer 15 composed of a sheet of flexible, thermally insulative, polymeric foam, such as a foam sheet composed of a crosslinked polyethylene modified with ethylene vinyl acetate copolymer. Additionally, it is further desirable that the interior surface of the foam layer be continuously bonded to an interior fabric layer 17, which fabric layer is preferably composed of terrycloth or brushed nylon tricot. Provided the foam layer is flexible and thermally insulative, the selection of a particular chemical species or genus of the foam employed is not generally critical, however. Thus, foams based on polyester or polyether polyurethanes, foams based on polymers and copolymers of vinyl chloride, foams based on alpha-olefin polymers and copolymers and even true elastomeric foams, such as those formed from natural or synthetic rubbers, can often be found suitable for employment as the foam layer 15 of the invention. Thermoplastic foams are preferred, however, and a closed cell foam is preferred over an open celled foam for the layer 15, in part because of better insulative properties and, in part, because closed cell foams do not readily imbibe body fluids, such as perspiration, or cleansing fluids, such as water, and will thus be more hygienic and more readily dried after washing of the cuff. The interior panel 5 of the construction can conveniently be in the nature of a layer 19 of a fabric such as flannel or terrycloth.

Generally, but particularly where the therapeutic thermal cuff construction of the invention is to be utilized in the treatment of the legs or large domestic animals subject to vehicle transport or subject to maintenance in stalls, another preferred embodiment of the invention resides in the selection of a polymeric foam material for the layer 15 of exterior panel 3 which is absorptive of physical shock. Such foams convert a substantial portion of impact energy imposed thereupon into heat and are viscoelastic, not elastic, in behavior. The use of such a foam material for the layer 15, of course, confers additional protection of the affected body member against further injury, such as due to jostling encountered in the transport of such animals or due to the animal's kicking of its enclosure if fractious or nervous in temperament. Indeed, even where the animal does not require therapeutic thermal treatment of any sort, nevertheless use of this preferred embodiment of the cuff of the invention may be conveniently and beneficially resorted to simply as a protective measure during transport of the animal or during enclosure of the animal in its stall. In human applications, of course, use of the preferred impact absorptive viscoelastic foams for the layer 15 can also protect the body member from further accidental injury. Such impact absorbing foams are well known and are characterized by a high material loss factor and a marked tendency to recover their original shape and dimensions slowly, rather than elastically, when a deforming stress is removed therefrom. Among such energy absorptive polymeric foam materials are, for instance, a predominantly closed cell polyvinylchloride foam sold under the trade designation, E-A-R ® C-3002, by Cabot Corporation, E-A-R Division, Indianapolis, Ind.; a polyurethane foam sold under the trade designation, SORBOTHANE ®, by Sorbothane Inc., Kent, Ohio; latex modified slow recovery polyurethane foams made in accordance with U.S. Pat. No. 4,158,087 to Louis L. Woot, June 12, 1979; acrylic latex impregnated polyurethane foams made in accordance with U.S. Pat. No. 4,008,350, to George H. Crawford et al., Feb. 15, 1977, and the like.

Figure 7:
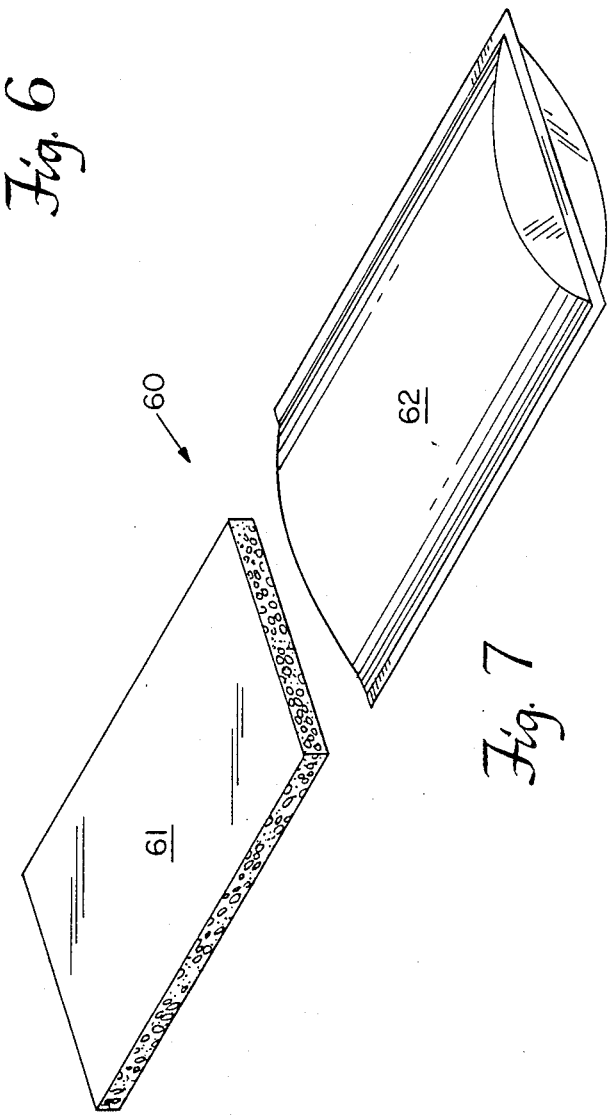
FIG. 7 is a schematic, diagrammatic, sectional side view of an impact energy absorbing viscoelastic polymeric foam pad assembly utilized in another preferred embodiment of the invention.

In FIG. 7 hereof there is shown an impact energy absorbing viscoelastic polymeric foam pad assembly 60 comprising a viscoelastic foam pad element 61 and a heat sealed thermoplastic film envelope 62 which receives said pad element 61 therein. The pad assembly 60 is of a size and thickness about that of the packet 20 and may be substituted therefor when it is desired that the cuff of the invention be utilized solely for impact protective, rather than therapeutic, purposes. Such viscoelastic polymeric foam pad assemblies 60 can also be utilized to advantage where the foam layer 15 of envelope 1 is not itself composed of an impact energy absorptive polymer foam. When utilized in consort with the thermally active packets 20, of course, the pad assembly& 60 is loaded into the pouch to the exterior of its companion packet 20. The envelope 62 may be conveniently composed of a polymer film material similar to or the same as that utilized for the construction of packet 20 or envelope 40, although other thermoplastic film materials may also be utilized, if desired. In order to avoid confusion as to the various packages or packets of materials contemplated for use in the present invention, the exteriors of said packages or packets may be color coded or imprinted with the contents, thereby to assure that proper order thereof is preserved when loaded into the pouches 7.

As alluded to previously, one of the essential features of the exterior panel 3, comprising the insulative polymeric foam layer 15, is that at least those portions thereof overlying and defining the exterior of each pouch 7 be quilted in pattern adapted to foster flexibility at least in the direction of wrap of the cuff around the body member to be treated. Said quilting can, of course, be accomplished by such means as stitching. However, in utilizing the preferred thermoplastic foam layer 15 of envelope 1, the fabric layers 13 and 17 and the foam layer 15 can be conveniently continuously thermally bonded together utilizing a low melting point thermoplastic adhesive film, such as low density polyethylene, interposed therebetween and the resulting laminated structure readily thermoformed such as to form distinct concavities 6 defining the packet 20-receiving pouches 7 and the quilting pattern 4. In FIGS. 1, 3, and 4 the quilting pattern 4 shown is composed of parallel and spaced apart quilt lines 8. During such thermoforming the thermoplastic foam layer will tend to collapse and densify to a greater or lesser extent under the influence of the heat and pressure applied locally thereto. In this regard, it should be borne in mind that this increase in density of the polymeric foam of layer 15 during thermoforming can, if carried to extremes, result in a substantial loss of the original insulative value of said foam layer 15, particularly in those areas overlying the pouches 7 and underlying the quilting pattern 4. Therefore, it is desirable that the thermoforming of the concavities 6 and the quilting pattern 4 be carefully controlled so as to minimize this densification of the foam layer 15. For similar reasons it is desirable that the total surface area of the thermoformed quilting lines 8 of the quilting pattern 4 be kept as small as possible, consistent, of course, with providing the envelope 1 structure with sufficient flexibility as to be readily wrapped around the body member to be treated. I have found, for instance, that the width of the quilting lines 8 should desirably be as narrow as practicable so as to avoid the creation of substantial thermal "shorts" through the exterior panel 3. In the embodiment shown in FIGS. 1, 3 and 4, as mentioned, the quilting pattern provides spaced apart, parallel quilting lines 8 which are oriented normal to the intended direction of wrap of the cuff. This, of course, provides substantial flexibility of the envelope 1 in the direction of wrap of the cuff around the intended body member. Additionally, I find it preferable that the quilting pattern 4 involve only those portions of the exterior panel 3 which overlie the pouches 7, it generally being the case that the flexibility of those portions of envelope 1 lying outside the areas of pouches 7 will be adequate without quilting thereof.

Figure 8:
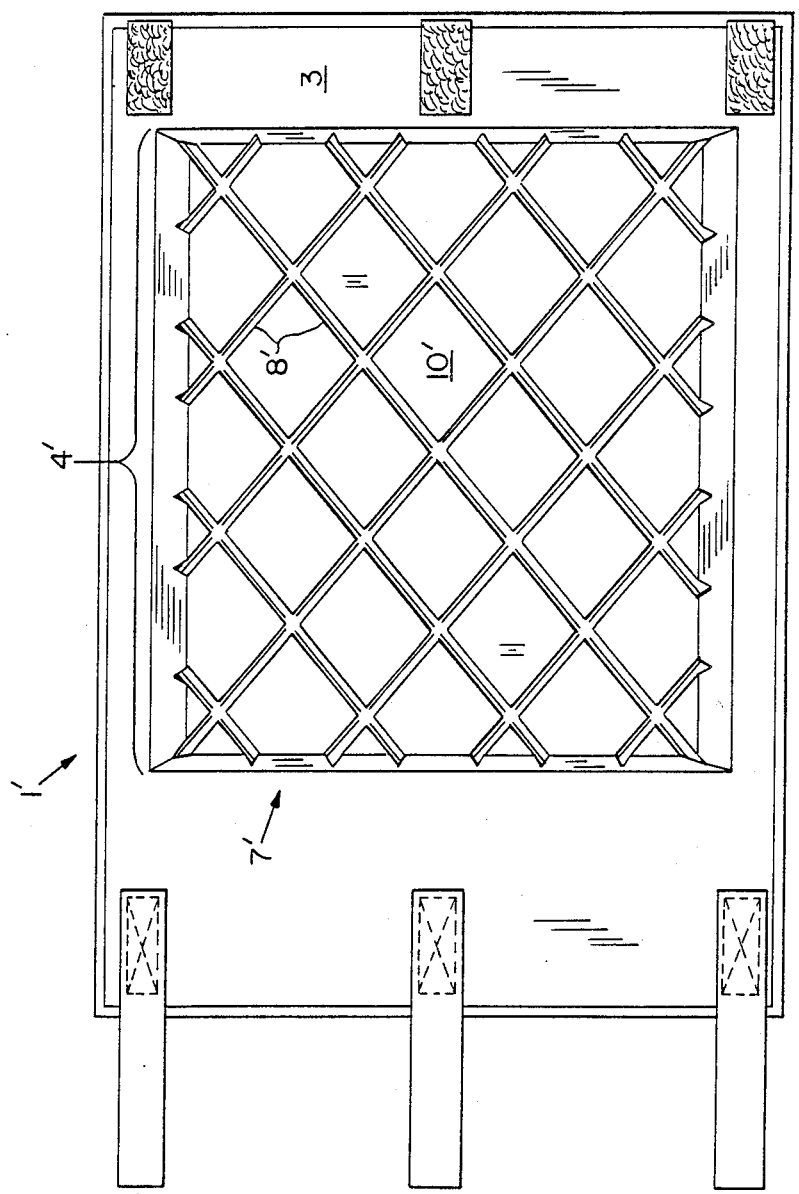
FIG. 8 is a schematic, diagrammatic, plan view of the exterior side of another embodiment of the therapeutic thermal cuff of the invention disclosing a diamond shaped quilting pattern of that portion of the exterior panel overlying the pouch.

The quilting pattern described above is useful for treatment of body members not involving a joint or articulation or when a joint or articulation is involved, but it is desired to restrict motion of that joint during thermal treatment thereof. However, where it is desired that some freedom of motion of the joint be preserved during the thermal treatment of such a body part, the quilting pattern shown in FIG. 8 hereof can be useful. In said FIG. 8 there is shown an envelope 1' having an exterior panel 3' wherein that portion of said panel 3' overlying the pouch 7' is composed of quilting lines 8' arranged in a diamond shaped quilting 4'. One opposed pair of apices of each of the diamonds 10' is oriented normal to the direction of wrap while the other opposed pair is oriented parallel to the direction of wrap. This arrangement, of course, provides substantial flexibility of the panel 3' both in the direction of wrap and normal thereto. Accordingly, the diamond shaped quilting pattern 4' can be found useful to employ in the therapeutic thermal cuff construction of the invention when the cuff is intended to be employed for thermal treatment of body members involving a joint or articulation such as for knees, elbows, ankles, wrists and the like of humans, or the corresponding body members of domestic animals.

Other factors involving the foam layer 15 can also affect the flexibility of the exterior panel 3 of the envelope 1, such factors including the thickness of the foam layer 15, the composition of the foam employed and the density thereof. Generally speaking, I prefer that the thickness of the foam layer 15 in the completed construction not be substantially greater than about 5/8 inch (15.9 mm) and, even more preferably, not greater than ½ inch (12.7 mm). At layer 15 thicknesses greater than about 5/8 inch (15.9 mm) the resulting envelope 1 construction can be excessively stiff. With respect to composition, it is well known that the chemical structure of the polymer employed for the foam, including the use of flexibilizers or plasticizers, internal or external, car have a marked affect on the stiffness of foams prepared therewith. For instance, where crosslinked polymers are employed, the greater the crosslink density of the polymer the stiffner will be the resulting foam. In such polymers as polyurethanes, polyether polyol starting materials tend to yield more flexible foams than do polyester polyol starting materials of the same or similar molecular weight and structure. Also, the greater the ratio of urethane to urea linkages in the finished polymer the greater will be the flexibility of the resulting foam. The use of plasticizers is common in the formulation of flexible foams. Indeed, in the ethylene/vinyl acetate copolymer modified crosslinked polyethylene foams which I have found to be particularly useful as the foam layer 15 of the invention, the vinyl acetate monomer functions as an internal plasticizer in the composition. Accordingly, the concentration of the vinyl acetate moiety in this copolymer composition can have a profound effect on the ultimate flexibility of such foams. Also, at a given thickness of the foam layer 15, the greater the density of a foam of a particular chemical composition the less the flexibility thereof. Suffice it to say, therefore, that the inherent flexibility of polymeric foams is subject to a number of factors well known to those of skill in the art. Such factors may be taken into account at the outset of the practice of the present invention or may be readily resolved by a small number of trial and error experiments utilizing a few candidate foams in the preparation of a proposed cuff in accordance with the invention.

Another factor which can affect the flexibility of the panel 3 is the fabric employed as the interior layer 17. I have found that when the interior layer 17 of panel 3 comprises a loosely woven or loop pile fabric, such as a brushed nylon tricot or a polyester, cotton or polyester/cotton blend terrycloth, a significant contribution to the overall flexibility of the panel 3 can result.

Completing the general construction of the envelope 1 is the provision of suitable means for securing the cuff in the wrapped condition around the affected body member. Said securing means can take the form of, for instance, tie or adhesive tabs, separate and distinct tie tapes, elastic loop fasteners, or the like. Preferably, however, the securing means for the envelope 1 will be in the nature of elongate hook 18 and loop 18' fastener tapes of the type mentioned previously with respect to the closure means 11 for the pouches 7. A plurality of such hook 18/loop 18' fastener tapes are secured in cooperative and spaced relationship to the respective ends of the envelope 1. Additionally, a binding 16 may be secured, such as by stitching or thermal bonding, around the periphery of the envelope 1, thereby to protect the edges of the fabric exterior layer 13, the polymeric foam layer 15, the interior fabric layer 17 and the interior fabric panel 5.

Figure 5:
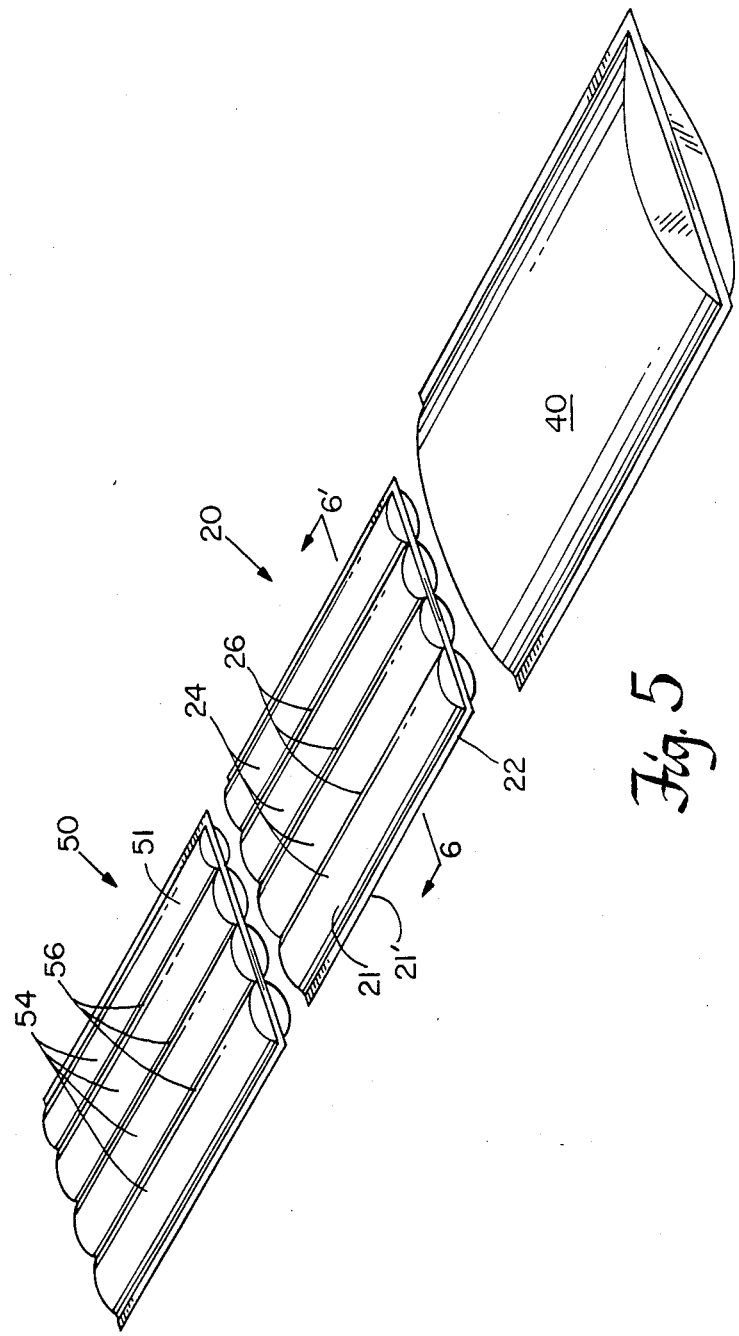
FIG. 5 is a schematic, diagrammatic, exploded perspective view of a preferred embodiment of the invention wherein the heat of fusion composition-containing packet is heat sealed within an envelope of a tough, abrasion resistant, thermoplastic polymer film and wherein said packet is utilized in consort with another packet containing a heat storage material.
Figure 6:
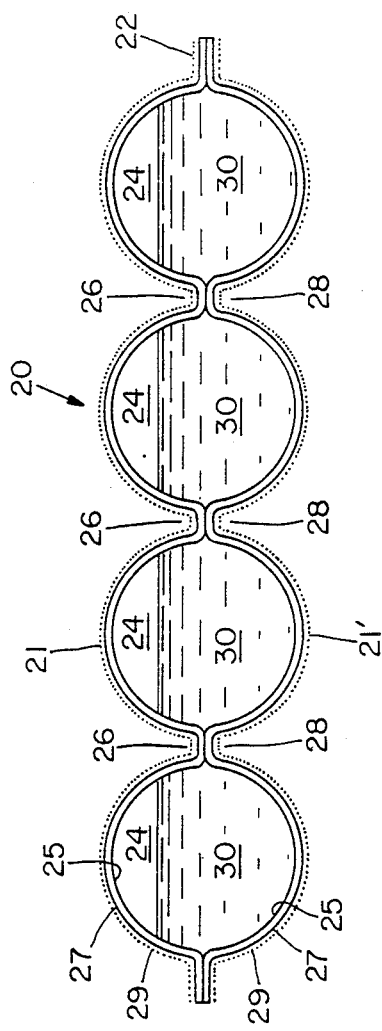
FIG. 6 is a schematic, diagrammatic, sectional side view of the heat of fusion composition-containing packet 20 of FIG. 5, taken through lines 6—6' thereof.

Referring now particularly to FIGS. 4, 5 and 6 hereof, each heat of fusion composition-containing packet 20 comprises a container composed of opposed thermoplastic polymeric film sheets 21, 21', heat sealed together at (i) the peripheries thereof to define a continuous perimeter flange 22 and (ii) spaced apart parallel quilt lines 26 which are oriented in a direction normal to the intended direction of wrap of the completed cuff assembly. Said flange 22 and quilt lines 26, therefore, segment the packet 20 into a number of separate and distinct chambers 24, each said chamber 24 being articulatingly affixed to its neighboring chamber 24 by narrow webs 28 of heat sealed thermoplastic film material therebetween. Said quilt lines 26 serve to provide the packet 20 with sufficient flexibility to allow the packet 20 to accommodate itself to the curvature of the cuff as it is wrapped around the body member to be treated. In constructing the packet 20, the bottom and side edges are heat sealed together to form a portion of the flange 22, as are the quilt lines 26, thereby defining a container whose multiple chambers 24 are open at the upper ends thereof. The chambers 24 are then filled with the selected heat of fusion composition and the remaining upper edge of the packet then heat sealed to complete the closure of the packet 20 and the remainder of the perimeter flange 22. If desired, the quilt lines 26 of the packet 20 can be arranged in a diamond shaped array, similar to that of the panel 3' shown in FIG. 8, thereby conferring a similar benefit of flexibility in two directions of motion to the resulting packet 20. Generally, however, it will be found that the heat of fusion composition contents 30 and, therefore, the packet 20 containing same, is adequately flexible under the usual conditions of use such that an array of parallel, spaced apart quilt lines 26, as shown in FIGS. 4, 5 and 6, will usually be adequate.

Suitable thermoplastic film materials for construction of the packet 20 are generally any thermoplastic polymer film which is chemically and physically inert to the heat of fusion composition contained therein under the conditions of use thereof. Alpha-olefin polymer films, particularly polyethylene and polypropylene based films, have been found generally suitable. In addition, there are many composite multi-layer thermoplastic film or sheet materials commercially available which can be usefully and beneficially employed in the construction of the packets 20 of the invention. In general, such multi-layer thermoplastic films or sheets have one or more useful properties conferred thereto by each of the layers thereof. Referring now specifically to FIG. 6, I have found that a ternary multi-layer thermoplastic sheet material having a nominal overall thickness of about 4 mils (0.101 mm) and composed of a polyethylene layer 25 of 3.25 mils (0.082 mm) thickness, an intermediate polyamide layer 27 of 0.75 mil (0.019 mm) thickness and an essentially immeasurably thin polyvinylidene chloride coating 29 to constitute an excellent material of construction for the packet 20. The polyethylene layer 25 is readily heat sealed, the polyamide layer 27 confers substantially improved strength to the overall construction and the polyvinylidene chloride coating 29, although of extreme thinness, confers substantially reduced water vapor transmission properties to the overall construction. In constructing the packet 20 from this material, the opposed sheets 21, 21' of the polymeric material film are oriented with the polyethylene layers 25 facing one another. This having been done, the heat sealing to form the flange 22 and quilt lines 26 is accomplished in the manner already outlined above.

In another preferred embodiment of the invention, shown in FIGS. 4 and 5, the packet 20, containing the heat of fusion composition, is received in an envelope 40 composed of a tough, abrasion resistant, heat sealed thermoplastic film material. In this embodiment additional protection of the packet 20 and the heat of fusion composition 30 contents thereof is provided by the envelope 40. I have found that a good material of construction for the protective envelope 40 consists of a thermoplastic polyurethane film having a thickness of about 4 mils (0.101 mm). Said material exhibits excellent abrasion resistance, and, should any of the chambers 24 of packet 20 suffer a failure, the heat of fusion composition 30 thereof will continue to be fully contained within the envelope 40. As in the construction and preparation of the packet 20, three sides of the envelope 40 are heat sealed together, the packet 20 inserted in the open end of the envelope, preferably under mild vacuum in order to minimize air entrapment between the envelope 40 and the packet 20, and the remaining open side of the envelope 40 heat sealed together to complete the closure thereof.

Suitable heat of fusion compositions 30 are generally compounds and mixtures of compounds which crystallize in passing from their molten state to their solid or semi-solid state. Amongst such compounds are organic and inorganic crystalline salts, particularly hydrated inorganic salts, and various crystalline polymers. Specific examples of such compounds are: cadmium nitrate tetrahydrate (50.5° C.), calcium nitrate tetrahydrate (42.6° C.), cobalt nitrate hexahydrate (57° C.), cupric nitrate hexahydrate (24.4° C.), ortho-phosphoric acid (42.4° C.), hypo-phosphoric acid (62° C.), sodium thiosulfate (48.5° C.) and the like. The principal considerations regarding the heart of fusion composition to be employed are the latent heat content of the composition and the temperature range of the phase change thereof whereat the generation or use of heat by the fusing or crystallizing composition takes place. Certain compositions are more efficient than others in terms of the heat produced or extracted per unit weight of the composition. With respect to the question of the phase change temperature range of the composition, since most homeothermic mammals, including humans, have normal temperatures within the range of 32° to 39° C., the fusion temperature range for the heat of fusion composition 30 for therapeutic cooling purposes will reside in a range substantially below this range, say, between −10° and 25° C. and, preferably, between 4° C. and 8° C. For therapeutic heating purposes the fusion temperature range of the composition 30 will reside within the range of between about 40° and 70° C., preferably between 48° C. and 52° C. I generally prefer as the heat of fusion composition polyethylene glycols because they are readily available commercially in various molecular weight fractions of considerably different fusion or phase change temperature ranges and have relatively high latent heats of fusion. There follows a table showing the average molecular weight and fusion or phase change temperature ranges for a series of commercially available polyethylene glycols manufactured and sold under the brandname, CARBOWAX ®, by Union Carbide Company, Danbury, Conn.

| Trade Designation | Molecular Weight | Phase Change Temp. (°C.) |
| --- | --- | --- |
| CARBOWAX ® 300 | 285–315 | −15 to −8 |
| CARBOWAX ® 400 | 380–420 | 4 to 8 |
| CARBOWAX ® 600 | 570–630 | 20 to 25 |
| CARBOWAX ® 1000 | 950–1050 | 37 to 40 |
| CARBOWAX ® 1450 | 1300–1600 | 43 to 46 |
| CARBOWAX ® 3350 | 3000–3200 | 54 to 58 |
| CARBOWAX ® 8000 | 7000–9000 | 60 to 63 |

From the foregoing table, then, it is clear that polyethylene glycols offer substantial flexibility in the selection of an appropriate composition within the desired phase change or fusion temperature ranges. Where an intermediate temperature range is desired, it is, of course, possible to blend two or more grades or molecular weight fractions of the polyethylene glycols to arrive at a composition having the desired fusion or phase change temperature range or to arrive at a composition wherein the phase change, and thus the generation or extraction of heat, occurs over a broader temperature range than by use of a single grade of the material. Moreover, because the polyethylene glycols are substantially miscible with water, it is also possible to control the phase change temperature of these polymeric glycols by compounding thereof with water. For instance, the CARBOWAX 8000 glycol shown above can be mixed with water to a concentration of about 14%, total weight, to result in a useful phase change composition for the purposes of the present invention. If desired, the heat of fusion compositions 30 utilized in the present invention may also contain nucleating agents, crystal growth inhibiting agents and other beneficial modifiers or adjuvants known in the art.

Where the desired therapeutic thermal treatment is in the nature of cooling a body member, yet another preferred embodiment of the invention is depicted in FIG. 5. Said embodiment involves the use of a supplemental packet 50, containing a heat storage material, in corsort with the packet 20, containing the heat of fusion composition 30. The packet 50 comprises a container 51, of similar or the same construction as that used for the packet 20 and comprising multiple heat sealed chambers 54 whose spaced apart parallel quilting lines 56 are also oriented normal to the direction of the wrap of the cuff. Said chambers 54 are filled with a heat storage material. While not a requisite of the invention, it is preferred that the packets 20 and 50 be loaded together into the envelope 40 and the envelope 40 then sealed. Where this is accomplished, it is necessary to mark the exterior of the envelope 40 in a manner such as to identify the relative locations of the packets 20 and 50 therewithin. This can be done by utilizing a particular color for the side of the envelope containing the packet 20 or 50 and another color for the other side. Alternatively, the envelope 20 can simply be marked on the side containing the packet 20 with "interior" and on the side containing the packet 50 with "exterior" or other suitable indicia. Alternatively, but less desirably, the packet 50 can be provided with a separate heat sealed envelope therefor or envelopes need not be provided for either of the packets 20 or 50. In any event, when this embodiment of the invention is utilized, the packets 20 and 50 are first cooled to below the phase change temperature of the composition 30 and are then loaded into the pouches 7 of envelope 1, the packet 50 being disposed intermediate the packet 20 and the foam layer 15 of the exterior panel 3. Thus, there is established a heat transfer relationship between the outer side of the packet 20 and the inner side of packet 50. Since water has a very high heat storage capacity, is abundantly available and is economic, it is the heat storage material of choice for the packet 50. If desired, water can be utilized in admixture with antifreeze compounds such as alcohols or glycols. However, such admixtures will necessarily result in a heat storage composition of lesser heat storage capacity than water, alone. It is the role of the heat storage packet 50 to accept and store heat from the heat of fusion composition 30 as said composition itself extracts heat from the treated body member, thereby prolonging the cooling effect of the heat of fusion composition 30 and prolonging the duration of the phase change of said heat of fusion composition. We have found, surprisingly, that the provision of the packet 50, acting in consort with the packet 20, prolongs the heat extraction efficiency of the packet 20 in the cuff environment to a degree substantially beyond that achieved when the mass of the heat of fusion material 30 in packet 20 is simply increased by the amount of mass of the heat storage material contained in the packet 50.

Again in the instance where cooling of a body member is contemplated, another preferred embodiment of the invention is depicted in FIG. 4. Therein there is provided a relatively thin flat heat sealed thermoplastic polymer envelope 70 containing an antifreeze solution, such as ethylene glycol, alcohol, salt or sugar dissolved in water said solution having a sufficient concentration of the antifreeze component therein as to have a freezing point substantially below that of the heat of fusion composition 30 utilized in the packet 20. As is shown, the envelope 70 is positioned in the pouch 7 so as to be interposed between the interior panel 5 and the heat of fusion containing packet 20. It is in the nature of things that heat of fusion compositions, when cooled to below their fusion temperatures, solidify into semisolid masses. When the packet 20 is the element closest to the panel 5, said "frozen" semisolid masses may initially be perceived by the patient as uncomfortable, particularly so because the injured body member treated with the invention will usually be sensitive to physical contact of any sort. Of course, upon extraction of sufficient heat from the treated body member, the heat of fusion composition will pass through its phase change and be converted to a liquid, thereby fully relieving whatever discomfort the patient may have initially perceived upon application of the cuff to the body member. In accordance with the embodiment of the invention disclosed above, however, the antifreeze contents of the envelope 70 remain in a fluid state throughout the entire treatment of the affected body member, thereby to function as a soft, compliant cushion for the body member from the outset of the treatment.

Obviously, many changes, modifications and alterations may be made in the above description without departing from the essential spirit and scope of the invention. For instance, the size, and geometry of the envelope 1 the number and sizes of pouches 7 and the number and sizes of packets 20 containing the heat of fusion composition 30 are subject to obvious variations depending upon the specific use and the body member to be treated with the therapeutic thermal cuff of the invention. Indeed, the cuff of the invention can be made large enough to treat an entire human or animal body, such as is often desirable when treating a dangerously febrile patient by cooling or when treating a hypothermia victim by warming of the entire body. Where the cooling embodiment of the invention is contemplated utilizing a heat storage material in consort with the heat of fusion composition, it is obvious that a single integral packet may be employed, with suitable partitioning thereof into inner and outer chambers, rather than the separate and distinct packets 20 and 50 described hereinbefore. The heat of fusion composition 30 will be loaded into the inner chambers of the integrated packet and the heat storage material loaded into the outer chambers thereof. Accordingly, it is intended, and should be so understood, that the foregoing description is to be regarded as illustrative of the principles of the invention and of certain embodiments thereof and not in a limiting sense.

The embodiment of the invention is which an exclusive property or privilege is claimed are defined as follows:

1. A therapeutic thermal cuff for treating a body member comprising:
 (A) an envelope comprising an exterior panel having affixed thereto an interior panel, said exterior panel comprising a flexible thermally insulative foam layer and said interior panel being composed of a fabric layer, said interior and exterior panels being affixed to one another so as to define at least one pouch therebetween, each said pouch being adapted to receive therein a thermally active packet, that portion of said exterior panel overlying each said pouch being quilted with a plurality of spaced apart quilt lines in an array adapted to provide flexibility of said cuff in the intended direction of wrap of the cuff around a body member to be treated therewith; and
 (B) a thermally active packet for each said pouch, each said thermally active packet comprising a container composed of opposed polymeric film sheets sealed together to form a plurality of spaced apart quilt lines in an array adapted to provide flexibility of said packet in the intended direction of wrap of the cuff around a body member to be treated therewith, said quilt lines additionally segmenting said container into a plurality of separate and distinct chambers, each said chamber being articulatingly affixed to neighboring chambers by a thin web of polymeric film material; each said chamber containing a heat of fusion composition therein, said heat of fusion composition having a heat of fusion temperature selected to either extract heat from a body member as said composition is heated by the body member and transitions from its solid state to its liquid state, or provide heat to a body member as said composition is cooled by the body member and transitions from its liquid state to its solid state.

2. The cuff of claim 1 wherein said exterior panel comprises an exterior fabric layer continuously bonded to the exterior surface of said foam layer.

3. The cuff of claim 2 wherein said exterior fabric layer is composed of an interlocked woven polyester fabric.

4. The cuff of claim 1 wherein said exterior panel comprises an interior fabric layer continuously bonded to the interior surface of said foam layer.

5. The cuff of claim 4 wherein said interior fabric layer is a brushed nylon tricot or a terrycloth.

6. The cuff of claim 1 wherein said foam layer of said exterior panel is composed of a polymeric foam composition having impact energy absorbing, viscoelastic properties.

7. The cuff o claim 1 wherein said polymeric foam layer of said exterior panel is composed of a closed cell foam.

8. The cuff or claim 1 wherein said polymeric foam layer of said exterior panel has a thickness of no greater than about 5/8 inch (15.9 mm).

9. The cuff of claim 1 wherein said polymeric foam layer is composed of a thermoplastic polymer.

10. The cuff of claim 9 wherein said thermoplastic polymer is a crosslinked polyethylene modified with an ethylene/vinyl acetate copolymer.

11. The cuff of claim 9 wherein said exterior panel is thermoformed to form a concavity to define each said pouch.

12. The cuff of claim 9 wherein said exterior panel is thermoformed to define said quilt lines.

13. The cuff of claim 9 wherein said exterior panel is thermoformed to form a concavity to define each said pouch and said quilt lines thereof.

14. The cuff of claim 1 wherein the fabric of said interior panel is a terrycloth or flannel.

15. The cuff of claim 1 wherein each said pouch comprises a slot, said slot being of a length sufficient to receive said thermally active packet therethrough.

16. The cuff of claim 15 wherein each slot of said interior panel includes closure means therefor.

17. The cuff of claim 16 wherein said closure means comprises a hook and loop tape fastener.

18. The cuff of claim 1 including securing means for securing said cuff in the wrapped condition around a body member treated therewith.

19. The cuff of claim 18 wherein said securing means comprises hook and loop fastener tapes cooperatively secured to the exterior of said envelope.

20. The cuff of claim 1 wherein said quilt lines of said exterior panel are arranged in spaced apart, parallel array and are oriented normal to the intended direction of wrap of the cuff around a body member to be treated therewith.

21. The cuff of claim 1 wherein said quilt lines of each thermally active packet are arranged in spaced apart, parallel array and are oriented normal to the intended direction of wrap of the cuff containing said packet around a body member to be treated therewith.

22. The cuff of claim 1 wherein said quilt lines of said exterior panel are arranged in a diamond shaped pattern, one opposed pair of apices of each diamond being oriented normal to the intended direction of wrap of the cuff around a body member to be treated therewith while the other opposed pair of apices is oriented in the intended direction of wrap of the cuff around said body member.

23. The cuff of claim 1 wherein each polymeric film sheet of said thermally active packet is a multi-layer composite sheet comprising a layer of polyethylene, an intermediate layer of a polyamide and, disposed over said intermediate layer, thin coating of polyvinylidene chloride, wherein the opposed layers of said sheets are the polyethylene layers thereof and wherein the seal of said packet and the quilt lines thereof are formed by heat sealing together portions of the facing polyethylene layers of said sheets.

24. The cuff of claim 1 wherein each said thermally active packet is housed in a sealed envelope composed of a tough abrasion resistant polymeric film material.

25. The cuff of claim 24 wherein said material is polyurethane.

26. The cuff of claim 1 wherein the heat of fusion composition contained in said thermally active packet has a heat of fusion temperature of between about $-10°$ C. and about 25° C.

27. The cuff of claim 1 wherein the heat of fusion composition contained in said thermally active packet has a heat of fusion temperature of between about 40° C. and about 70° C.

28. The cuff of claim 1 wherein said heat of fusion composition comprises polyethylene glycol.

29. The cuff of claim 28 wherein said heat of fusion composition comprises a solution of polyethylene glycol and water.

30. The cuff of claim 28 wherein said heat of fusion composition comprises a blend of polyethylene glycols of differing molecular weight fractions.

31. The cuff of claim 28 wherein said heat of fusion composition has a heat of fusion temperature of between about 4° C. and about 8° C.

32. The cuff of claim 28 wherein said heat of fusion composition has a heat of fusion temperature range of between about 48° C. and about 52° C.

33. The cuff of claim 1 wherein each said thermally active packet contains a heat of fusion composition whose heat of fusion temperature is selected to cool a body member and wherein there is provided another packet to be insertable in the pouch between said thermally active packet and said exterior panel to establish a heat exchange relationship with said thermally active packet, said other packet containing a heat storage material.

34. The cuff of claim 33 wherein said heat storage material comprises water.

35. The cuff of claim 24 wherein, in addition to said thermally active packet, there is also provided in said sealed tough abrasion resistant polymeric film envelope another packet containing a heat storage material, said other packet being in heat exchange relationship with said thermally active packet, said sealed envelope being adapted to be received into said pouch with the thermally active packet oriented to the side of the interior panel and said other packet being oriented to the side of the exterior panel of said pouch.

36. The cuff of claim 1 wherein each said thermally active packet contains a heat of fusion composition whose heat of fusion temperature is adapted to cool a body member and wherein there is additionally provided a relatively thin sealed polymeric film envelope containing an antifreeze solution, said envelope being insertable in said pouch in heat exchange relationship with said thermally active packet and being interposed between said packet and the interior panel of said cuff envelope, said antifreeze solution having a solidification temperature substantially below the fusion temperature of said heat of fusion composition, said antifreeze solution-containing envelope thereby functioning as a fluid filled cushion between said thermally active packet and a body member.

37. The cuff of claim 36 wherein said antifreeze solution comprises ethylene glycol and water.

38. The cuff of claim 1 including, for each pouch thereof, an impact energy absorbing element comprising a polymeric foam pad having dimensions similar to those of said thermally active packet, said pad being composed of an impact energy absorbing, viscoelastic polymeric foam.

39. The cuff of claim 38 wherein each said impact energy absorbing element comprises said pad contained in a sealed polymeric film envelope.

* * * * *